United States Patent [19]

Esche, Jr. et al.

[11] Patent Number: 5,405,544
[45] Date of Patent: Apr. 11, 1995

[54] ASHLESS ANTIWEAR-ANTIOXIDANT LUBRICATING OIL ADDITIVE

[75] Inventors: Carl K. Esche, Jr., Wappingers Falls; Julian H. Dancy, Poughkeepsie; Doris Love, Fishkill, all of N.Y.

[73] Assignee: Texaco Inc., White Plains, N.Y.

[21] Appl. No.: 100,803

[22] Filed: Aug. 2, 1993

Related U.S. Application Data

[63] Continuation-in-part of Ser. No. 872,213, Apr. 22, 1992, abandoned.

[51] Int. Cl.$^6$ ............... C10M 137/10; C10M 135/20
[52] U.S. Cl. ........................... 252/46.6; 252/46.7; 558/177; 558/186; 558/194
[58] Field of Search ............... 558/177, 186, 194; 252/46.7, 46.6

[56] References Cited

U.S. PATENT DOCUMENTS

| | | | |
|---|---|---|---|
| 2,568,784 | 9/1951 | Woodstock | 260/2 |
| 3,042,703 | 7/1962 | Schegk et al. | 558/194 |
| 3,197,404 | 7/1965 | Berger et al. | 252/32.7 |
| 3,346,667 | 10/1967 | Firth | 260/920 |
| 3,683,054 | 8/1972 | Wollensak et al. | 558/194 |
| 3,991,141 | 11/1976 | Beriger et al. | 558/194 |
| 4,834,893 | 5/1989 | Doner et al. | 252/32.7 E |
| 5,037,567 | 8/1991 | Farng et al. | 252/46.7 |

FOREIGN PATENT DOCUMENTS 499453  8/1992  European Pat. Off.

*Primary Examiner*—Ellen M. McAvoy
*Attorney, Agent, or Firm*—George J. Darsa

[57] ABSTRACT

Beta-hydroxyalkyl-bis(alkylthiomethylphenyl) dithiophosphate esters represented by the formulas

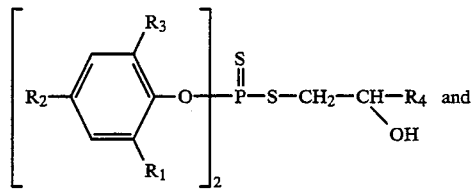

and

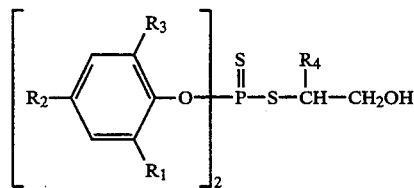

wherein $R_1$, $R_2$ and $R_3$ are each H, a ($C_1$–$C_{40}$) alkyl group, —$CH_2SR$, —$C_6H_5$ or —$C_6H_4$—$R_5$ providing at least one of $R_1$, $R_2$ and $R_3$ is —$CH_2SR$; $R_4$ is H or a ($C_1$–$C_{40}$) alkyl group; R is H or a ($C_1$–$C_{40}$) alkyl group, —$C_6H_5$ or —$C_6H_4$—$R_5$; and $R_5$ is a ($C_1$–$C_{40}$) alkyl group.

5 Claims, No Drawings

ASHLESS ANTIWEAR-ANTIOXIDANT LUBRICATING OIL ADDITIVE

CROSS-REFERENCE TO RELATED APPLICATIONS

This is a continuation-in-part application of U.S. patent application Ser. No. 07/872,213, filed Apr. 22, 1992, now abandoned.

BACKGROUND OF THE INVENTION

This invention is related to lubricating oils, and more particularly to an ashless, antiwear-antioxidant lubricating oil additive.

In developing lubricating oils there have been many attempts of providing additives which impart antiwear-antioxidant properties in the lubricating oils. Zinc dithiophosphates have been used in formulated motor oils as antiwear-antioxidant additives for more than fifty years. However, zinc dithiophosphates give rise to ash which contributes to particulate matter found in automotive exhaust emissions. It is important to limit the particulate matter formed during engine use for toxicological and environment reasons, but it is equally important to maintain undiminished antiwear-antioxidant properties of the lubricating oil.

Thus, it is an object of this invention to provide an ashless, antiwear-antioxidant additive which imparts these desired properties to a lubricant.

DISCLOSURE STATEMENT

U.S. Pat. No. 2,568,784 discloses a method of producing reaction products of olefine oxides and phosphoric anhydride or phosphorus pentasulfide and the method of forming the same. The reaction products are prepared by reacting either phosphoric anhydride or phosphorus pentasulfide with an olefine oxide.

U.S. Pat. No. 3,197,404 discloses a method of producing reaction products of phosphorus pentasulfide with epoxides and metal salts thereof. These reaction products and salts are useful in lubricating oil compositions.

U.S. Pat. No. 3,346,667 discloses a reaction product produced from a phosphorus oxide or sulfide, an oxirane compound and a hydroxy or thiol compound together. These products are useful in synthetic plastics.

U.S. Pat. No. 4,834,893 discloses phosphorodithioate substituted carboxylic anhydride or acid derivates and their corresponding metal salts have been found to be effective multifunctional additives for various lubricants and fuels.

SUMMARY OF THE INVENTION

This invention provides beta-hydroxyalkyl-alkylthiomethyl phenyl-dithiophosphate esters represented by the formulas

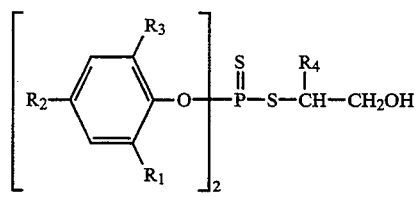

-continued

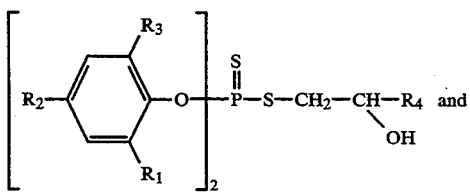

wherein $R_1$, $R_2$ and $R_3$ are each H, a ($C_1$–$C_{40}$) alkyl group, —$CH_2SR$, —$C_6H_5$ or —$C_6H_4$—$R_5$ providing at least one of $R_1$, $R_2$ and $R_3$ is —$CH_2SR$; $R_4$ is H or a ($C_1$–$C_{40}$) alkyl group; R is a ($C_1$–$C_{40}$) alkyl group, —$C_6H_5$ or —$C_6H_4$—$R_5$; and $R_5$ is a ($C_1$–$C_{40}$) alkyl group.

DETAILED DESCRIPTION OF THE INVENTION

The present invention relates to the use of ashless antiwear-antioxidant agents in lubricating oils to reduce the ash content of the formulation. The ashless materials will be used as either a partial or complete replacement for the zinc dithiophosphates currently used for antiwear-antioxidant purposes.

Up to the present time, alkylthiomethylphenols have not been used to (or disclosed herein) prepare dithiophosphoric acids. In the subsequent reaction of the corresponding dithiophosphoric acid with an epoxide, a product is formed with antiwear-antioxidant properties.

According to the present invention, an ashless, antiwear-antioxidant lubricating oil additive is produced by the method which comprises:

(a) reacting an alkylthiomethylphenol with phosphorus pentasulfide to form a dithiophosphoric acid intermediate;

(b) treating the dithiophosphoric acid intermediate with an expoxide to yield a corresponding dithiophosphoric ester alcohol product; and (c) recovering the ester alcohol product lubricating oil additive.

In the present method, alkylthiomethylphenol is reacted with phosphorus pentasulfide in a ratio of about 4:1 to give the corresponding dithiophosphoric acid. The dithiophosphoric acid is reacted with an epoxide in a ratio of about 0.5:1 to about 1.5:1 to give the corresponding alcohol derivatives (i.e., the ester alcohol product).

The equations for the reactions to produce the beta-hydroxyalkyl-bis(alkylthiomethylphenyl) dithiophosphateesters (I) and (II) are as follows:

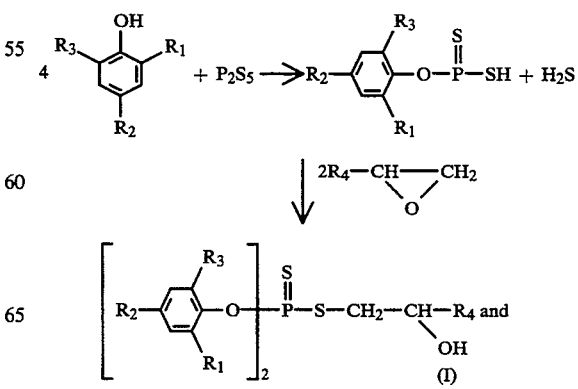

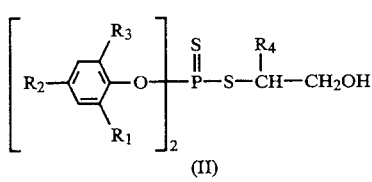

(II)

wherein $R_1$, $R_2$ and $R_3$ are each H, a ($C_1$–$C_{40}$) alkyl group, —$CH_2SR$, —$C_6H_5$ or —$C_6H_4$—$R_5$ providing at least one of $R_1$, $R_2$ and $R_3$ is —$CH_2SR$; $R_4$ is H or a ($C_1$–$C_{40}$) alkyl group; R is a ($C_1$–$C_{40}$) alkyl group, —$C_6H_5$ or —$C_6H_4$—$R_5$; and $R_5$ is a ($C_1$–$C_{40}$) alkyl group.

In the present method, the preferred alkylthiomethylphenols used are represented by the following formulas:

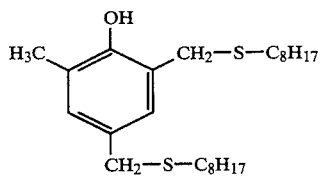

2-methyl-4,6-bis[(octylthio)methyl]phenol

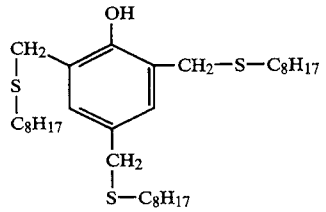

2,4,6-tris[(octylthio)methyl]phenol

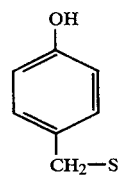

Mono-octylthiomethylphenol

According to the present invention, the alkylthiomethylphenol is added to a slurry of $P_2S_5$ in heptane at 70° C. (150° F.). The mole ratio of this alkylphenol to $P_2S_5$ is about 4:1 but could be in a range of about 5:1 to about 3:1. The mixture is stirred 1 hour at 70° C., 1 hour at 80° C., and 3 hours at 90° C. The unreacted $P_2S_5$ is then filtered off.

The dithiophosphoric acid and the epoxide are combined at an ambient temperature in a ratio of about 1:1, but could be in a range of about 0.5:1 to about 1.5:1. The mixture is then stirred at 90° C. for 3 hours, vacuum stripped and filtered.

The dithiophosphate esters that may be produced by the present method include 2-hydroxyalkyl- di[2-methyl-4,6-bis(octylthiomethyl) phenyl]-dithiophosphate represented by the formula

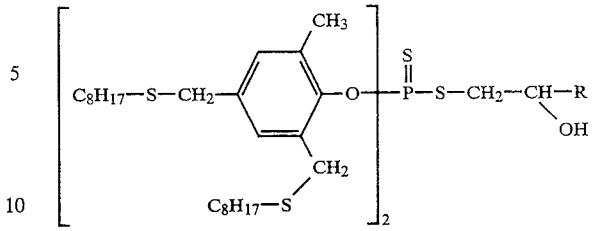

2-hydroxyalkyl-di-[2,4,6-tris-(octylthiomethyl) phenyl] dithiophosphate represented by the formula

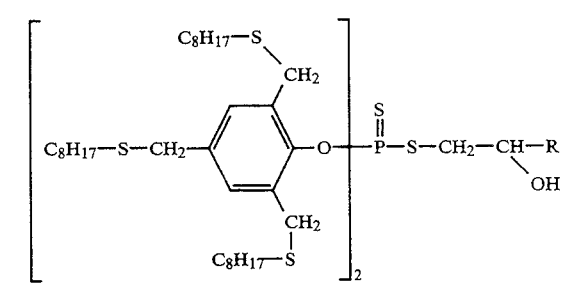

2-hydroxyalkyl-di-(monooctylthiomethylphenyl)-dithiophosphate represented by the formula

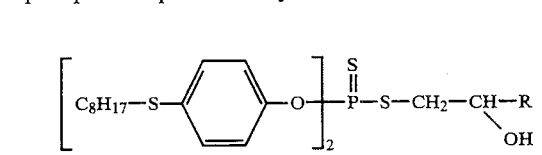

wherein the above formulas R is H or a ($C_1$–$C_{40}$) alkyl group.

In order to illustrate and show the advantages of the present invention, the following examples are provided.

EXAMPLE I

Preparation Of Dithiophosphoric Ester Alcohol From 2-Methyl-4,6-Bis[(Octylthio) Methyl] Phenol And A ($C_{18}$) Epoxide

MATERIALS 106.5 gms. (0.25 m) 2-methyl-4, 6-bis[(octylthio) methyl] phenol
14.0 gms. (0.0625 m) $P_2S_5$
100 ml heptane
37.25 gms (0.125 n) $C_{18}$ epoxide

PROCEDURE (1) Slurry of $P_2S_5$ in heptane prepared and heated to 70° C. (158° F.) under $N_2$ blanket (50 ml/min).

(2) The phenol added batchwise over ½ hours keeping temperature between 65° and 70° C. (149°–158° F.).

(3) Reaction stirred at 70° C. for one hour (4) Reaction stirred at 80° C. for one hour (5) Reaction stirred at 90° C. for three hours (6) Cooled and filtered. Filter cake washed with heptane. Washings added to filtrate.

(7) Entire filtrate and $C_{18}$ epoxide combined at ambient temperature.

(8) Stirred under $N_2$ (100 ml/min) and heated to 90° F. (194° F.).

(9) Stirred under $N_2$ at 90° C. for three hours to complete reaction and produce derivative.

(10) Derivative stripped to 90° C. under water-pump vacuum and kept there until no more solvent came over.

(11) Filtered to provide 102 grams of dithiophosphoric ester alcohol derivative (156 gms theory).

Product analyzed as follows:

| TESTS | FOUND | THEORY |
| --- | --- | --- |
| % S | 14.8 | 15.4 |
| % P | 2.59 | 2.5 |
| IR | — | — |
| Neut. No. | 2 | 0 |

EXAMPLE II

Preparation Of Dithiophosphoric Ester Alcohol From Monooctylthiomethylphenol And A ($C_{18}$) Epoxide

MATERIALS 63.5 gms (0.25 m) monooctylthiomethylphenol
14.0 gms. (0.0625 m) $P_2S_5$
100 ml heptane
37.25 gms. (0.125 m) $C_{18}$ expoxide

PROCEDURE (1) Slurry of $P_2S_5$ in heptane prepared and heated to 70° C. (158° F.) under $N_2$ blanket (50 ml/min).

(2) The phenol added batchwise over ½ hour, keeping temperature between 65° and 70° C. (149°–158° F.).

(3) Reaction stirred at 70° C. for one hour.

(4) Reaction stirred at 80° C. for one hour.

(5) Reaction stirred at 90° C. for three hours.

(6) Cooled and filtered. Filter cake washed with heptane. Washings added to filtrate.

(7) Entire filtrate and $C_{18}$ epoxide combined at ambient temperature.

(8) Stirred under $N_2$ (100 ml/min) and heated to 90° F. (194° F.).

(9) Stirred under $N_2$ at 90° C. for three hours to complete reaction and produce derivative.

(10) Derivative stripped to 90° C. under water-pump vacuum and kept there until no more solvent came over.

(11) Filtered to provide 88 grams of dithiophosphoric ester alcohol derivative (113 gms theory).

Product analyzed as follows:

| TESTS | FOUND | THEORY |
| --- | --- | --- |
| % S | 11.3 | 14.1 |
| % P | 2.96 | 3.4 |
| IR | — | — |
| Neut. No. | 26 | 0 |

EXAMPLE III

Preparation Of Dithiophosphoric Ester Alcohol From 2-Methyl-4,6-Bis [Octylthio)Methyl]Phenol And A ($C_{10}$) Epoxide

MATERIALS 106.5 gms (0.25) 2-methyl-4,6-bis [octylthio)methyl]phenol
14.0 gms. (0.0625 m) $P_2S_5$
100 ml. heptane
22.55 gms. (0.125 m) $C_{10}$ epoxide

PROCEDURE (1) Slurry of $P_2S_5$ in heptane prepared and heated to 70° C. (158° F.) under $N_2$ blanket (50 ml/min).

(2) The phenol added batchwise over ½ hour, keeping temperature between 65° and 70° C. (149°–158° F.).

(3) Reaction stirred at 70° C. for 1 hour.

(4) Reaction stirred at 80° C. for 1 hour.

(5) Reaction stirred at 90° C. for 3 hours.

(6) Cooled and filtered. Filter cake washed with heptane. Washings added to filtrate.

(7) Entire filtrate and $C_{10}$ epoxide combined at ambient temperature.

(8) Stirred under $N_2$ (100 ml/min) and heated to 90° F. (194° F.).

(9) Stirred under $N_2$ at 90° C. for three hours to complete reaction and produce derivative.

(10) Derivative stripped to 90° C. under water-pump vacuum and kept there until no more solvent came over.

(11) Filtered to provide 121 grams of dithiophosphoric ester alcohol derivative (141 gms theory).

Product analyzed as follows:

| TESTS | FOUND | THEORY |
| --- | --- | --- |
| % S | 15.6 | 15.4 |
| % P | 2.85 | 2.7 |
| IR | — | — |
| Neut. No. | 11 | 0 |

EXAMPLE IV

Preparation Of Dithiophosphoric Ester Alcohol From 2,4,6-Tris[(Octylthio)Methyl]Phenol And A ($C_{18}$) Epoxide

MATERIALS 86.0 gms. (0.150 m) 2,4,6-tris[(octylthio) methyl]phenol
8.3 gms. (0. 0375 m) $P_2S_5$
100 ml heptane
22.3 gms. (0. 075 m) $C_{18}$ epoxide

PROCEDURE (1) Slurry of $P_2S_5$ in heptane prepared and heated to 70° C. (158° F.) under $N_2$ blanket (50 mo/min).

(2) The phenol added batchwise over ½ hour, keeping temperature between 65° and 70° C. (149°–158° F.).

(3) Reaction stirred at 70° C. for 1 hour.

(4) Reaction stirred at 80° C. for 1 hour.

(5) Reaction stirred at 90° C. for 3 hours.

(6) Cooled and filtered. Filter cake washed with heptane. Washings added to filtrate.

(7) Entire filtrate and $C_{18}$ epoxide combined at ambient temperature.

(8) Stirred under $N_2$ (100 ml/min) and heated to 90° F. (194° F.).

(9) Stirred under $N_2$ at 90° C. for three hours to complete reaction and produce derivative.

(10) Derivative stripped to 90° C. under water-pump vacuum and kept there until no more solvent came over.

(11) Filtered to provide 89 grams of dithiophosphoric ester alcohol derivative (115 gms theory).

Product analyzed as follows:

| TESTS | FOUND | THEORY |
|---|---|---|
| % S | 14.7 | 14.6 |
| % P | 1.84 | 2.0 |
| IR | — | — |
| Neut. No. | 17 | 0 |

The following are data from tests to illustrate the effectiveness of the present lubricant additives.

Test Data Showing That The Epoxide Derivatives of Thioalkylated Phenols Are Antioxidants All additives were evaluated in a Bench Oxidation Test (BOT). In the BOT, the additive (1.0 or 0.5 wt %), overbased sulfonate (0.18% Ca) and SNO-150 were heated to 175° C. under $N_2$ and a sample taken (baseline). The mixture was then stirred at 175° C. under a stream of air at 500 ml/min. for six hours. Samples were taken every hour and the DIR of each sample was determined against the baseline at 1712 $cm^{-1}$. The six hour DIR was used as a measure of oxidation; the smaller the value, the better the antioxidant properties.

| | SIX HOUR DIR | | |
|---|---|---|---|
| Sample | No Additive | 1.0 wt % Additive | 0.5 w % Additive |
| SNO-150 + Overbased Sulfonate + No Additive | 22.0 | | |
| SNO-150 + Overbased Sulfonate + Ex. I Additive | " | 6.28 | 11.49 |
| SNO-150 + Overbased Sulfonate + EX. II Additive | " | 2.57 | 7.00 |
| SNO-150 + Overbased Sulfonate + EX. III Additive | " | 2.23 | 10.34 |
| SNO-150 + Overbased Sulfonate + EX. IV Additive | " | 2.30 | 2.62 |
| SNO-7 + Overbased Sulfonate + Commercial Antioxidant | " | — | 14.81 |
| SNO-150 + Overbased Sulfonate + Zinc Dithiophosphate | " | 6.14 | — |

Test Data Showing That The Epoxide Derivative of Thiomethylated Phenols Are Antiwear Agents The wear performance of the antiwear additives were evaluated in a Roxana Four-Ball Wear Tester, using 12.7 mm chrome alloy steel balls. Tests were run at 600 rpm, 40 kg load and 200 F. for 30 minutes. Test samples were prepared by adding the experimental antiwear agent and a pro-wear contaminant to an SAE 30 base blend containing dispersant, detergent, and antioxidant. The blends were prepared by adding sufficient experimental additive to obtain the desired phosphorus level (0.05 or 0.14 &P) and sufficient pro-wear contaminant to provide differentiation. The pro-wear contaminant used represents one found in engine service and enables good discrimination between antiwear additives in a short test. The average wear scar diameter of each sample was measured at each concentration. Test results are reported below in mm average wear scar diameter. All those additives that showed decreases in wear scar diameter of the level of the known antiwear agent would be good antiwear agents.

| Four Ball Wear Screening Test Avg. Wear Scar Diameter (MM) | | |
|---|---|---|
| Sample | 0.14% P | 0.05% P |
| Known Good Antiwear Agent | 0.39 | 0.65 |
| EX. I Additive | 0.33 | 0.43 |
| EX. II Additive | 0.38 | 0.53 |
| EX. III Additive | 0.40 | 0.46 |
| EX IV Additive | 0.36 | 0.48 |
| Poor Antiwear Agent | 0.54 | 0.62 |

We claim:

1. Beta-hydroxyalkyl-bis(alkylthiomethyl phenyl) dithiophosphate esters represented by the formulas

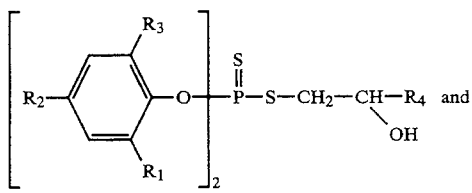

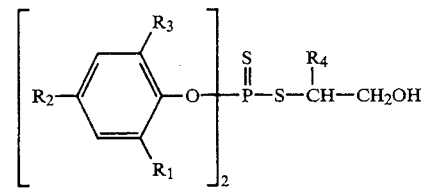

wherein $R_1$, $R_2$ and $R_3$ are each H, a ($C_1$-$C_{40}$) alkyl group, $-CH_2SR$, $-C_6H_5$ or $-C_6H_4-R_5$ providing at least one of $R_1$, $R_2$ and $R_3$ is $-CH_2SR$; $R_4$ is H or a ($C_1$-$C_{40}$) alkyl group; R is a ($C_1$-$C_{40}$) alkyl group, $-C_6H_5$ or $-C_6H_4-R_5$; and $R_5$ is a ($C_1$-$C_{40}$) alkyl group.

2. The esters of claim 1, wherein one of said esters is 2-hydroxyalkyl-di[2-methyl-4,6-bis(octylthiomethyl) phenyl]dithiophosphate represented by the formula

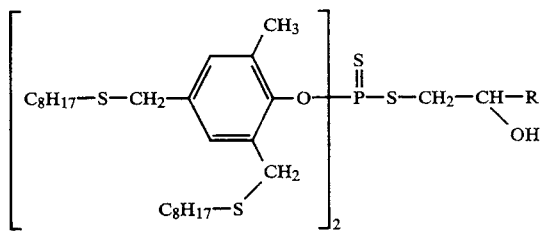

where R is H or a ($C_1$-$C_{40}$) alkyl group.

3. The esters of claim 1, wherein one of said esters is 2-hydroxyalkyl-di-[2,4,6-tris-(octylthiomethyl) phenyl]-dithiophosphate represented by the formula

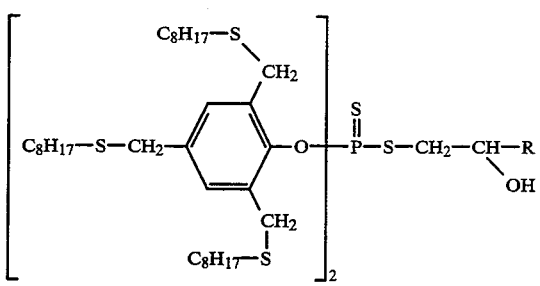

where R is H or a $(C_1-C_{40})$ alkyl group.

4. The esters of claim 1, wherein one of said esters is -2-hydroxyalkyl-di-(monooctylthiomethylphenyl)-dithiophosphate represented by the formula

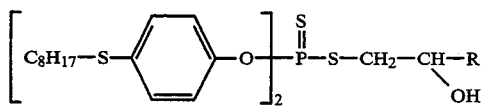

Where R is H or a $(C_1-C_{40})$ alkyl group.

5. An ashless antioxidant, antiwear lubricating oil additive represented by the formulas

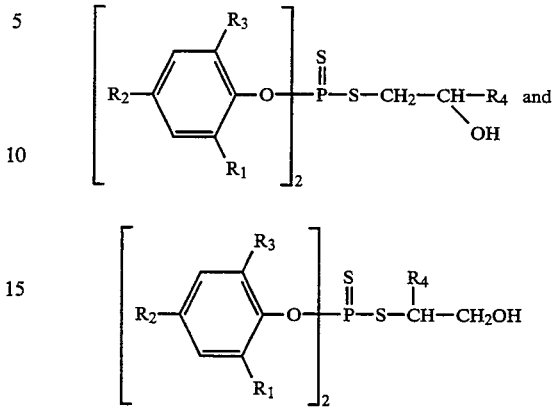

wherein $R_1$, $R_2$ and $R_3$ are each H, a $(C_1-C_{40})$ alkyl group, $-CH_2SR$, $-C_6H_5$ or $-C_6H_4-R_5$ providing at least one of $R_1$, $R_2$ and $R_3$ is $-CH_2SR$; $R_4$ is H or a $(C_1-C_{40})$ alkyl group; R is H or a $(C_1-C_{40})$ alkyl group, $-C_6H_5$ or $-C_6H_4-R_5$; and $R_5$ is a $(C_1-C_{40})$ alkyl group.

* * * * *